United States Patent [19]

Legutke et al.

[11] 4,265,837

[45] May 5, 1981

[54] PRODUCTION OF 1,2-DICHLOROETHANE

[75] Inventors: Günter Legutke, Brühl; Harald Scholz, Erftstadt; Kurt Schuchardt, Brühl, all of Fed. Rep. of Germany

[73] Assignee: Hoechst Aktiengesellschaft, Fed. Rep. of Germany

[21] Appl. No.: 33,817

[22] Filed: Apr. 27, 1979

[30] Foreign Application Priority Data

May 2, 1978 [DE] Fed. Rep. of Germany ....... 2819308

[51] Int. Cl.$^3$ ............................................. C07C 17/02
[52] U.S. Cl. ................................................... 570/243
[58] Field of Search ........... 260/659 A, 659 R, 656 R, 260/662 A

[56] References Cited

U.S. PATENT DOCUMENTS

| | | | |
|---|---|---|---|
| 3,637,895 | 1/1972 | Riegel et al. | 260/659 A |
| 4,028,427 | 7/1977 | Tsao | 260/659 A |
| 4,071,572 | 1/1978 | Amato et al. | 260/659 A |

FOREIGN PATENT DOCUMENTS

| | | |
|---|---|---|
| 1518930 | 7/1969 | Fed. Rep. of Germany . |
| 1518931 | 7/1969 | Fed. Rep. of Germany . |
| 1518932 | 7/1969 | Fed. Rep. of Germany . |
| 1618701 | 3/1974 | Fed. Rep. of Germany . |
| 2626133 | 12/1976 | Fed. Rep. of Germany . |
| 2742409 | 4/1978 | Fed. Rep. of Germany . |
| 2718878 | 11/1978 | Fed. Rep. of Germany . |

*Primary Examiner*—Winston A. Douglas
*Assistant Examiner*—J. V. Howard
*Attorney, Agent, or Firm*—Connolly and Hutz

[57] ABSTRACT

The invention provides a process for making 1,2-dichloroethane by subjecting ethylene to an oxychlorination reaction with hydrogen chloride and a gas containing molecular oxygen, in gas phase, at elevated temperature and in contact with a fluidized bed catalyst of copper-II-chloride on a carrier, wherein the reaction gases are cooled under pressure in two condensation stages, condensed 1,2-dichloroethane and water are removed, the bulk of unreacted starting gas and inert gas are recycled, the reaction gases coming from the second condensation stage are delivered to a third condensation stage, cooled therein under pressure down to a temperature within the range 5° to 18° C. and to the extent necessary to retain in the recycle gas 0.5 to 3 volume % of 1,2-dichloroethane, and the recycle gas is admixed, directly upstream of the reactor, with a quantity of pure oxygen necessary to replace consumed oxygen. The present process provides more specifically for preheated hydrogen chloride to be wholly or partially introduced into the recycle gas heated to 150° to 200° C. and for the latter to be then admixed with pure oxygen, the oxygen being admitted at a point lying between the hydrogen chloride feed point and the feed point of the recycle gas into the reactor.

4 Claims, 1 Drawing Figure

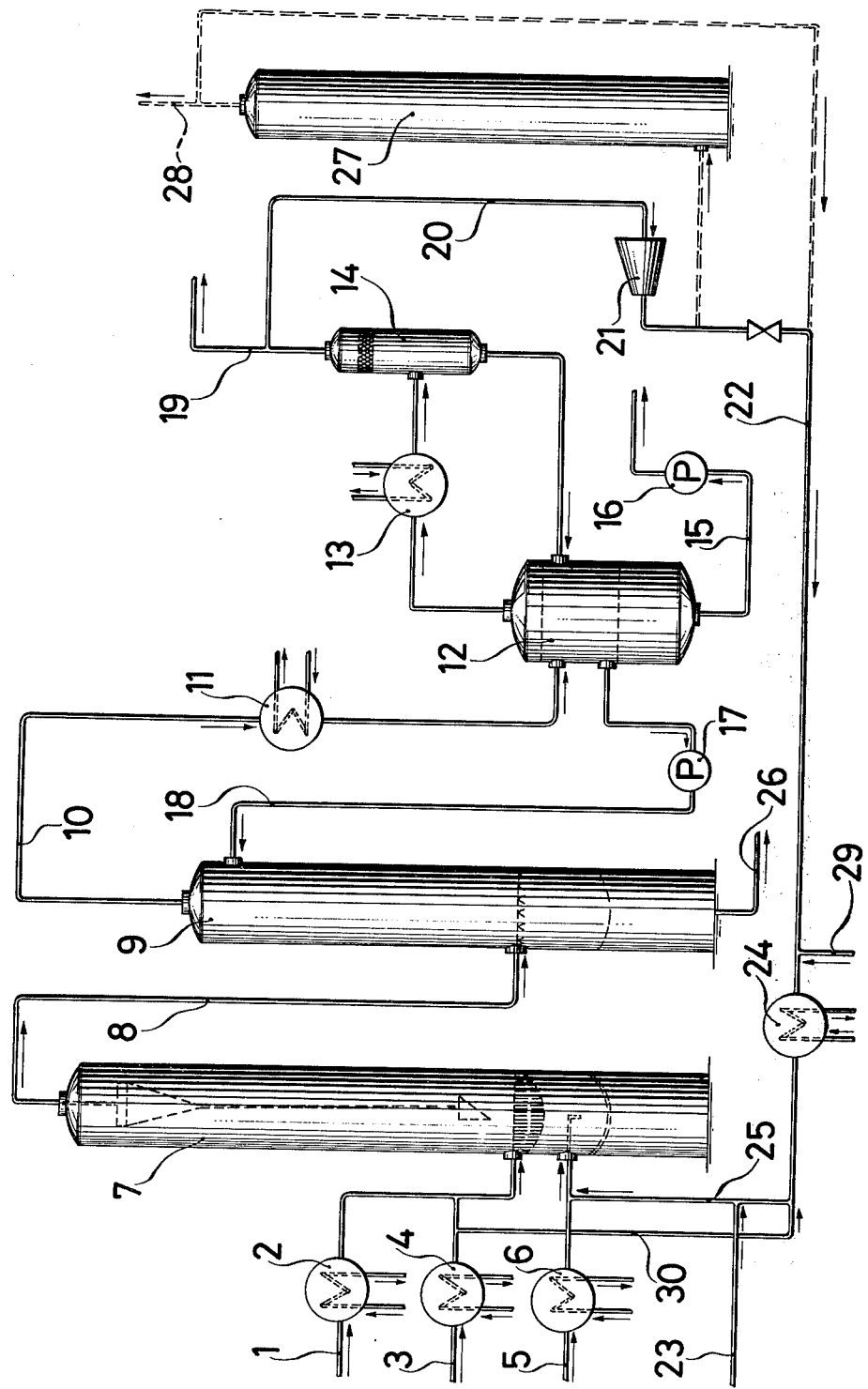

PRODUCTION OF 1,2-DICHLOROETHANE

This invention relates to a process for making 1,2-dichloroethane by subjecting ethylene to an oxychlorination reaction with hydrogen chloride and a gas containing molecular oxygen, preferably air, in gas phase at elevated temperature and in contact with a fluidized bed catalyst of copper-II-chloride on a carrier, wherein the reaction gases are cooled under pressure in two condensing stages, condensed 1,2-dichloroethane and water are removed, and the bulk of unreacted starting gas and inert gas are recycled.

This known oxychlorination reaction occurs in accordance with the following equation:

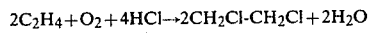

$$2C_2H_4 + O_2 + 4HCl \rightarrow 2CH_2Cl\text{-}CH_2Cl + 2H_2O$$

German Patent Specification "Auslegeschrift" No. 1,618,701 describes a process, wherein 1.6 to 2.5 mols of ethylene is reacted with 2.0 mols of hydrogen chloride and 0.6 to 1.0 mol of oxygen in the presence of 0.5 to 3.0 mols of carbon monoxide in contact with a copper-aluminum oxide catalyst, in contact with which the carbon monoxide is partially oxidized simultaneously to carbon dioxide. After condensation of the reaction products, it is necessary to recycle the unreacted starting materials, for reasons of economy. In order to enable the fluidized bed to be maintained, it is necessary to have a constant level of CO in the recycle gas. To this end, CO is oxidized to $CO_2$ above the catalyst made by a special process, and the resulting $CO_2$ is removed from the recycle gas by scrubbing the latter with a sodium hydroxide solution.

This process is not fully satisfactory in respect of the following points: (a) during the introduction of pure oxygen, special measures have to be taken as a precaution against spontaneous decomposition which may be caused by too high a content of ethylene and carbon monoxide and (b) it is necessary to scrub the recycle gas so as to free it from the carbon dioxide formed by oxidation. Next, it is necessary to recover separately dichloroethane and further chlorinated hydrocarbons from the scrubbing water.

Further processes have been described in German Patent Specifications "Auslegeschriften" Nos. 1,518,930; 1,518,931 and 1,518,932, wherein ethylene, oxygen and hydrogen chloride which are used in a molar ratio of (1.02 to 1.2) to (0.5 to 1.0) to 2.0, are reacted at 200° to 250° C. under a pressure of 0.7 to 3.5 bars in contact with a fluidized bed catalyst of $CuCl_2$ and $Al_2O_3$. In a first condensation stage, the reaction gases are cooled down to 70° to 100° C. and, in a second condensation stage, to 0° to 40° C. Incondensable gas portions are freed from residual 1,2-dichloroethane by scrubbing with an organic solvent and dichloroethane is ultimately recovered therefrom in a desorption column. The scrubbed gases which continue to contain fractions of chlorinated hydrocarbons and the organic solvent are either incinerated or allowed to escape into the atmosphere.

Coupled with the preferential use, in the process just described, of air as the oxygen carrier is the formation of important quantities of issuing gas containing only minor proportions of combustible compounds so that an additional fuel, e.g. fuel oil, has to be used in order to maintain the issuing gas at the temperature necessary for combustion.

Under the air pollution legislation of to-day, it is substantially not permissible for issuing gas containing chlorinated and other hydrocarbons, e.g. solvents, to be directly delivered to the atmosphere. The invariable loss of ethylene, dichloroethane and organic solvents which is associated therewith is a further adverse effect to consider and which adds to the difficulties encountered in the handling of important quantities of issuing gas.

A further cyclic process for making 1,2-dichloroethane by subjecting ethylene to an oxychlorination reaction has been described in U.S. Pat. No. 4,071,572, wherein 80 to 98 volume % of incondensable unscrubbed gas is recycled. The recycle gas contains about 0.1 to 10 volume % each of ethylene and oxygen and less than 20 volume % of 1,2-dichloroethane, 2 to 20 volume % of recycle gas being removed during each cycle. The reaction gases are successively cooled first down to 81°–121° C. in a cooling tower, then down to 32° to 49° C. in a first condenser, and ultimately down to 27° to 38° C. in a second condenser, so as to be freed substantially from dichloroethane and water. Substantially pure oxygen is used as the oxidizing gas in the process just described.

In the process described in German Patent Specification "Offenlegungschrift" No. 2,626,133, the oxygen and starting reactant are jointly introduced into the reaction zone, which is hazardous as substantially pure oxygen is liable to come into contact with ethylene.

The composition indicated for the recycle gas in the working Example of that specification does not permit substantially pure oxygen to be added to the gas upstream of the reactor, as the gas would be liable to undergo ignition. The lower limit of explosion of such gas mixtures lies indeed at a very low level, namely at 3.0 to 6.0 volume %, taken as the sum of the combustible gases comprising ethylene, 1,2-dichloroethane, carbon monoxide and organic by-products, depending on the oxygen content of the respective gas mixture. This low limit of explosion, which is typical of ethylene, carbon monoxide, 1,2-dichloroethane and organic by-products, culminates in considerable difficulties which may well be one of the reasons why all of the recycle processes described heretofore have failed to gain commercial interest.

Further processes, which avoid the adverse effects of the prior art methods just discussed, have been disclosed in German Patent Specifications "Offenlegungsschriften" Nos. 2,718,878 and 2,742,40. These Patents describe more specifically processes for making 1,2-dichloroethane by subjecting ethylene to an oxychlorination reaction with hydrogen chloride and a gas containing molecular oxygen, preferably air, in gas phase at elevated temperature and in contact with a fluidized bed catalyst of copper-II-chloride on a carrier, wherein the reaction gases are cooled under pressure in two condensing stages, condensed 1,2-dichloroethane and water are removed, and the bulk of unreacted starting gas and inert gas are recycled, which substantially comprise: cooling the reaction gases in a third condensation stage under pressure down to a temperature within the range 5° to 18° C. and to the extent necessary to retain in the recycle gas 0.5 to 3 volume %, preferably 0.5 to 1.5 volume %, of 1,2-dichloroethane, and directly admixing, upstream of the reactor, the recycle gas with a quantity of pure oxygen necessary to replace consumed oxygen.

Further features of the processes described in German Patent Specifications "Offenlegungsschriften" Nos. 2,718,878 and 2,742,40 provide:

(a) for an overall content of combustible ethylene, 1,2-dichloroethane, carbon monoxide and organic by-products of less than 3 to 6 volume % (which is the lower limit of explosion for an oxygen content of 25 to 12 volume %), to be established in the recycle gas:
  (1) by using the ethylene, oxygen and hydrogen chloride starting reactants in a molar ratio of (1.00 to 1.10):(0.50 to 0.70):2.00
  (2) by oxidizing 50 to 100, preferably 60 to 90 mol % of the carbon monoxide to carbon dioxide in contact with the catalyst, and
  (3) by maintaining the necessary content of inert gas of the recycle gas by supplying it with the calculated quantity of air and/or inert gas.
(b) for the recycle gas to be first freed partially or completely from combustible ethylene, 1,2-dichloroethane, carbon monoxide and organic by-products, which are removed therefrom jointly or separately by means of a customary absorbend, and to be then admixed with pure oxygen;
(c) for the quantity of recycle gas to be maintained constant and for the catalyst bed to be fluidized uniformly by means of the said constant quantity of recycle gas;
(d) for the catalyst performance to be controlled by varying the content of oxygen in the recycle gas, upstream of the reactor, within the range 12 to 25 volume %;
(e) for the composition of the recycle gas admixed with oxygen to be continually monitored analytically;
(f) for the reaction gases to be cooled under pressure in a first condensation zone down to 70°-100° C. and in a second condensation zone down to 37° to 40° C.

Also disclosed in German Patent Specifications "Offenlegungsschriften" Nos. 2,718,878 and 2,742,409 is a special process for making 1,2-dichloroethane by subjecting ethylene to an oxychlorination reaction with hydrogen chloride and a gas containing molecular oxygen, preferably air, in gas phase at temperatures of 200°-250° C. and in contact with a fluidized bed catalyst of copper-II-chloride on a carrier, wherein the reaction gases are cooled under pressure in a first condensation stage to 70°-100° C. and in a second condensation stage to 0°-40° C., condensed 1,2-dichloroethane and water are removed, and the bulk of unreacted starting gas and inert gas are recycled, which process comprises: cooling the reaction gases in the second condensation stage to 37°-40° C., delivering them to a third condensation stage and cooling them therein under pressure down to a temperature within the range 5° to 18° C. and to the extent necessary to retain in the recycle gas 0.5 to 3 volume %, preferably 0.5 to 1.5 volume %, of 1,2-dichloroethane; and directly admixing, upstream of the reactor, the recycle gas with a quantity of pure oxygen necessary to replace consumed oxygen. In the process just described, the ethylene, oxygen and hydrogen chloride starting gases are preferably employed in a molar ratio of (1.00 to 1.04):(0.50 to 0.60):2.00 and the reaction is preferably effected under a pressure of 0.7 to 3.5 bars. The three condensation stages are maintained under the same pressure. The catalyst used in this prior process is, e.g. the $CuCl_2/Al_2O_3$-catalyst disclosed in German Patent Specification "Auslegeschrift" No. 1,518,932. The recycle gas is directly recycled to the reactor, i.e. it is left unscrubbed with sodium hydroxide solution.

The processed disclosed in German Patent Specification "Offenlegungsschriften" Nos. 2,718,878 and 2,742,409 provide for the reaction gas which has been freed from 1.2-dichloroethane to be recycled and for the recycle gas to be admixed with pure oxygen to make up for the oxygen consumed during the reaction. These are conditions which ensure that the gas mixture remains below its lower limits of explosion after admixture of the recycle gas with pure oxygen and temperature increase of the oxygen/recycle gas-mixture to about 150° C. Inasmuch as these limits are really at a low level, limited use can only be made of the technically beneficial higher concentration of 1,2-dichloroethane in the recycle gas, upstream of the reactor. This is the reason why it has been suggested in German Patent Specifications "Offenlegungsschriften" No. 2,742,409 that the recycle gas should be scrubbed with one or more aromatic hydrocarbons. In addition to this, these low limits of explosion do not permit the conversion rate of the reactants inside the reactor to be increased by increasing the proportion of oxygen in the recycle gas as the latter would then naturally more rapidly reach its critical composition.

In accordance with our present invention, we have now found that the methods described in German Patent Specifications "Offenlegungsschriften" Nos. 2,718,878 and 2,742,409 and the safety of operation can be favorably influenced by admitting the hydrogen chloride and pure oxygen through feed points other than disclosed in these specifications.

As compared with German Patent Specification "Offenlegungsschriften" Nos. 2,718,878 and 2,742,409, the present invention provides an improved process for making 1,2-dichloroethane by subjecting ethylene to an oxychlorination reaction with hydrogen chloride and a gas containing molecular oxygen, which comprises: introducing the preheated hydrogen chloride wholly or partially into the recycle gas heated to 150° to 200° C. and then admixing the recycle gas with pure oxygen, the oxygen being admitted at a point lying between the hydrogen chloride feed point and the feed point of the recycle gas into the reactor.

It is generally good practice to admix the recycle gas with oxygen having a temperature of 20° to 150° C. and to preheat the hydrogen chloride to a temperature of 150° to 200° C.

A preferred feature of the present process provides for a 10 to 30 volume % content of pure oxygen to be established in the recycle gas, the percentage being based on the overall quantity of gas comprising recycle gas, hydrogen chloride and oxygen.

The reaction which the reactants undergo in contact with the fluidized bed catalyst remains unchanged by admixing the recycle gas with hydrogen chloride in accordance with this invention. On the other hand, however, it is possible by the operational step just described to reduce the concentration of all gaseous constituents forming the recycle gas and in this way to render the latter even less explosive. A further beneficial effect of the present process resides in the fact that the recycle gas can be admixed with more pure oxygen than heretofore so that more effective use can be made of the capacity of an existing plant. By supplying more oxygen, the concentration of oxygen in the mixture of recycle gas and hydrogen chloride is but insignificantly increased inasmuch as oxygen and hydrogen chloride per se are used in a preselected ratio. In the prior art methods, it has been customary to preheat pure oxygen prior to combining it with the recycle gas. This can be dispensed with in the present process, which provides for cold oxygen to be added to a mixture of preheated recycle gas and preheated hydrogen chloride. The various gaseous constituents are mixed together in conventional manner, e.g. with the use of a Venturi nozzle structure.

The process of the present invention will now be described with reference to the accompanying drawing.

Ethylene coming from a conduit 1 and a first preheater 2 is introduced into a fluidized bed reactor 7. The latter 7 is either fed simultaneously with a portion of a preselected quantity of hydrogen chloride gas, which comes from a conduit 3 and a second preheater 4 and is mixed with ethylene (in this case the hydrogen chloride balance portion travelling through a conduit 30 is mixed with recycle gas coming from a conduit 25) or the overall quantity of hydrogen chloride coming from conduits 3 and 30 is added to the recycle gas coming from a conduit 25. By means of a conduit 5 and a third preheater 6, air is introduced into the reactor 7. Placed therein is a copper-II-chloride catalyst. The oxychlorination is exothermal. By means of a hot water circulation system, the temperature is maintained e.g. at 220° to 235° C. The pressure prevailing in the whole system is maintained at 3 bars. Via a cyclone, the gas is admitted through conduit 8 to first condensation stage 9, wherein it is cooled down to about 80° C. by means of reaction water which comes from separator 12 and is pumped by means of pump 17 through conduit 18. Unconsumed hydrogen chloride and the bulk of reaction water are condensed. Via a conduit 10 and a cooler 11 (second condensation stage), the gas is cooled down to about 40° C. 1,2-dichloroethane and residual water are condensed and coarsely separated from one another in the separator 12. The water is recycled to the first condensation stage 9, removed through a conduit 26 and worked up. Crude dichloroethane is taken from the separator 12 through a conduit 15 and a pump 16, and delivered to a purification stage. Uncondensed gas is cooled in a cooler 13 (third condensation stage) down to 5° to 18° C. to the extent necessary to retain 0.5 to 3 volume % of 1,2-dichloroethane therein. Post-condensed 1,2-dichloroethane is collected in a separator 14 and recycled to the separator 12. The remaining gas is recycled to the reactor 7 via a conduit 20, compressor 21, conduit 22, fourth preheater 24 and conduit 25. Prior to recycling the mixture of preheated recycle gas and hydrogen chloride gas, through the conduit 25 into the reactor 7, it is thoroughly admixed in conduit 25 with the quantity of oxygen of 20° to 150° C. (coming from conduit 23) necessary to establish a total $O_2$-content of 10 to 30 volume % in the mixture of hydrogen chloride, recycle gas and oxygen. It is also possible to provide, downstream of the compressor 21, an absorption facility 27 containing a liquid or solid absorbent, through which all uncondensed gas should conveniently be passed. The composition of the gas admixed with oxygen upstream of the reactor is continuously monitored analytically in order to avoid the formation of ignitable mixtures in the recycle gas. As soon as the necessary quantity of gas is available, the supply of air through the conduit 5 is throttled, e.g. the gas is admixed with the quantity of air necessary to maintain its content of nitrogen approximately constant. The quantity of gas is maintained constant by the removal, through conduit 19 or 28, of a quantity which substantially corresponds to the proportion of ethylene which undergoes combustion to CO and $CO_2$. The quantity of gas so removed is worked up in known manner. Conduit 29 is used for the introduction of inert gas. This can be controlled automatically depending on the gas composition which is continuously monitored.

In the following Examples, use was made of a fluidized bed reactor 3.0 meters wide and 29.9 meters high. The catalyst was a copper-II-chloride catalyst which contained about 4 weight % of copper and was deposited on aluminum oxide. The catalyst was used in an average quantity of 48.700 kilograms.

EXAMPLE 1

Ethylene, hydrogen chloride and oxygen (in the form of air), which were used in a molar ratio of 1.04 to 2.00 to 0.55 were heated separately to 145°–150° C. and admitted to the distributing tray of the reactor. The reactants underwent conversion substantially to 1,2-dichloroethane, while heat was set free, which was abstracted by cooling with water maintained under high pressure, and used for the generation of steam. The reactor was maintained at a temperature of 233° C. and under a pressure of 3 bars. The reaction gas was cooled by condensing it in three stages and condensed crude dichloroethane and water were obtained. In the third condensing stage, the gas was cooled down to about 17° C. The gas issuing from the third condensing stage was composed of, in volume %:

Oxygen, 8.0
Nitrogen, 33.3
Carbon monoxide, 2.5
Carbon dioxide, 53.0
1,2-dichloroethane, 2.1
Ethylene, 0.62
Further combustible ingredients, <0.5

The gas mixture contained altogether 5.72 volume % of combustible ingredients. This gas mixture (recycle gas) was compressed to 5.5 bars, heated to 166° C. and mixed with hydrogen chloride heated to 166° C. coming from conduit 30. By means of a standard mixer, the whole (recycle gas/hydrogen chloride-mixture) was further admixed with pure oxygen of 20° C. coming from conduit 23. Hydrogen chloride and oxygen were again metered in in the molar ratio of 2.00:0.55. Directly upstream of the reactor, the gas mixture of recycle gas, hydrogen chloride and oxygen had a temperature of 150° C., contained 13.8 volume % of oxygen and combustible ingredients in a total proportion reduced to 13.8 volume %.

The ethylene conversion rate was 99.82% and 1,2-dichloroethane was obtained in a yield of 96.72% of the theoretical, based on the quantity of ethylene. The catalyst performance was 280 g of 1,2-dichloroethane per kg of catalyst per hour.

EXAMPLE 2

The procedure was as in Example 1, but the quantity of hydrogen chloride admitted through conduit 30 was increased by 30 volume %. This permitted the quantity of oxygen metered in through conduit 23 to be also increased by 30 volume %. Directly upstream of the reactor, the gas mixture had a temperature of 150° C. and contained altogether 2.9 volume % of combustible substances. Its oxygen content was found to have been increased to 14.7 volume %. In order to maintain the molar ratio of ethylene/hydrogen chloride/oxygen of 1.04:2.00:0.55, it was necessary to increase equally by 30 volume % the quantity of ethylene which was admitted through conduit 1.

The ethylene conversion rate was 99.84% and 1,2-dichloroethane was obtained in a yield of 96.42% of the theoretical, based on the ethylene conversion rate. The catalyst performance was 360 g of 1,2-dichloroethane per kg of catalyst per hour.

We claim:

1. A process for making 1,2-dichloroethane by subjecting ethylene to an oxychlorination reaction with hydrogen chloride and a gas containing molecular oxygen, in gas phase, at elevated temperature and in contact with a fluidized bed catalyst of copper-II-chloride on a carrier, wherein the reaction gases are cooled under pressure in two condensation stages, condensed 1,2-dichloroethane and water are removed, the bulk of unreacted starting gas and inert gas are recycled, the reaction gases coming from the second condensation stage are delivered to a third condensation stage, cooled therein under pressure down to a temperature within the range 5° to 18° C. and to the extent necessary to retain in the recycle gas 0.5 to 3 volume % of 1,2-dichloroethane, and the recycle gas is admixed, directly upstream of the reactor, with a quantity of pure oxygen necessary to replace consumed oxygen, the improvement which comprises: introducing preheated hydrogen chloride wholly or partially into the recycle gas heated to 150° to 200° C. and then admixing the recycle gas with pure oxygen the oxygen being admitted at a point lying between the hydrogen chloride feed point into the recycle gas and the feed point of the recycle gas into the reactor.

2. A process as claimed in claim 1, wherein the pure oxygen admitted to the recycle gas has a temperature of 20° to 150° C.

3. A process as claimed in claim 1, wherein the hydrogen chloride is preheated to a temperature of 150° to 200° C.

4. A process as claimed in claim 1, wherein the recycle gas is admixed with a quantity of pure oxygen necessary for it to contain 10 to 30 volume % of $O_2$, based on the overall quantity of recycle gas, hydrogen chloride and oxygen.

* * * * *